United States Patent [19]

Qualeatti et al.

[11] 4,340,546
[45] Jul. 20, 1982

[54] PROCESS FOR THE REDUCTION OF UNSATURATED CARBOXYLIC ACIDS

[75] Inventors: Gail M. Qualeatti; Dalia Germanas, both of Des Plaines, Ill.

[73] Assignee: UOP Inc., Des Plaines, Ill.

[21] Appl. No.: 241,870

[22] Filed: Mar. 9, 1981

[51] Int. Cl.³ ............................................. C11C 3/12
[52] U.S. Cl. .................................. 260/409; 560/205; 560/225; 568/885; 260/410.9 N
[58] Field of Search ......... 260/409, 410.9 R, 410.9 N, 260/410.9 D; 560/205, 225

[56] References Cited

U.S. PATENT DOCUMENTS 3,123,626  3/1964  Kirsch ................................. 260/409

OTHER PUBLICATIONS

Chem. Absts. 82:P116749y; 71:P3049f; 72:R47921c.

Primary Examiner—John F. Niebling
Attorney, Agent, or Firm—James R. Hoatson, Jr.; Raymond H. Nelson; William H. Page, II

[57] ABSTRACT

Unsaturated carboxylic acids, as exemplified by oleic acid, erucic acid, crotonic acid, etc., may be subjected to a reduction reaction by treatment with hydrogen in the presence of a catalyst comprising cadmium and rhenium composited on a solid support such as alumina. The reduction reaction is effected at elevated temperatures and pressures, a specific feature of the reaction process being that hydrogen is continuously bled from the reactor during the reaction period. This feature results in obtaining a higher selectivity of esters and alcohols which retain the unsaturation of the original starting material.

11 Claims, No Drawings

PROCESS FOR THE REDUCTION OF UNSATURATED CARBOXYLIC ACIDS

BACKGROUND OF THE INVENTION

It is known that unsaturated carboxylic acids may be reduced to an ester or to the corresponding alcohol. However, the reducing catalysts which have heretofore been employed are not selective in the hydrogenation process, and thus the reductive process usually results in eliminating the retention of the unsaturation in the carbon chain. The compound which is obtained is therefore a saturated ester or alcohol. This is true when utilizing catalysts such as a mixture of copper and chromium oxide, rhenium catalysts which may be used in either a supported or unsupported state or which may also contain a noble metal of Group VIII of the Periodic Table, such as platinum, palladium or ruthenium.

In many instances, it is desirable to retain the unsaturation of the carbon chain when obtaining either alcohols or esters of the starting unsaturated carboxylic acid. As will hereinafter be shown in greater detail, it has now been discovered that a process for effecting the reduction of unsaturated carboxylic acids may be effected by utilizing certain catalytic compositions of matter and also by utilizing certain modifications of the process to obtain esters or alcohols of unsaturated carboxylic acids in which the double bonds present in the original acid are retained in the reaction product.

DETAILED DESCRIPTION OF THE INVENTION

This invention relates to a process for the reduction of unsaturated carboxylic acids. More specifically, the invention is concerned with a process for treating unsaturated carboxylic acids of the type hereinafter set forth in greater detail to effect a reduction of said acids in which the unsaturated bonds which are present in the original acid are retained in the product.

Unsaturated acid esters, or alcohols, especially those which possess a relatively long carbon atom chain, will find a wide variety of uses in the chemical field. The usaturated acid esters, as exemplified by oleyl oleate, may be used as a substitute for sperm whale oil which is becoming increasingly difficult to obtain. Sperm whale oil is used as a high grade lubricating oil for light machinery such as watches, clocks and scientific instruments as well as in heat treating and rustproofing. In addition to use as a lubricant, the esters which are obtained according to the process of this invention may also be used in cosmetics such as perfumes, colognes, bath oils, soaps, powders, etc. This is especially true in the case of relatively long chain unsaturated esters.

It is therefore an object of this invention to provide a process for the reduction of unsaturated carboxylic acids.

A further object of this invention is to provide a process for the reduction of an unsaturated carboxylic acid whereby the ester product resulting from the process will retain the unsaturation of the starting material.

In one aspect, an embodiment of this invention resides in a process for the reduction of an unsaturated carboxylic acid comprising treating an unsaturated carboxylic acid in a reaction system in the presence of hydrogen and a reduction catalyst at treatment conditions, continuously bleeding hydrogen from said reaction system during the reaction period, and recovering the resultant unsaturated product.

A specific embodiment of this invention is found in the process for the reduction of an unsaturated carboxylic acid which comprises treating oleic acid in a reaction system in the presence of hydrogen and a reduction catalyst comprising cadmium and rhenium composited on gamma-alumina, said process being effected at a temperature in the range of from about 100° to about 500° C., and a pressure in the range of from about 100 to about 5000 psi, continuously bleeding hydrogen from said reaction system during the reaction period, and recovering the resultant oleyl oleate, oleyl alcohol and their geometric and positional isomers.

Other objects and embodiments can be found in the following further detailed description of the present invention.

As hereinbefore set forth, the present invention is concerned with a process for the reduction of an unsaturated carboxylic acid in which said acid is treated with hydrogen in the presence of a reduction catalyst of the type hereinafter set forth in greater detail. By employing this catalyst, and also by employing certain reaction conditions, it is possible to obtain the resulting ester and/or alcohol in an amount in excess of that which has previously been obtained, as well as retaining the unsaturation in the carbon atom chain which is present in the starting material. As will hereinafter be shown in greater detail, by effecting a hydrogen bleed during the reaction, the product water which is formed during the reaction is continuously removed, thus permitting an enhanced activity and selectivity of the reaction to form the desired products.

Examples of unsaturated carboxylic acids which may be employed as starting materials to form the desired unsaturated esters will include those acids containing from 3 to about 22 carbon atoms, some specific examples of these acids being acrylic acids, the isomeric butenic acids such as crotonic acid, isocrotonic acid, vinyl acetic acid, methylacrylic acid, the isomeric pentenic acids such as tiglic acid, angelic acid, senecioic acid, the isomeric hexenoic acids, heptenoic acids, octenoic acids, nonenoic acids, decenoic acids, undecenoic acids, dodecenoic acids, tridecenoic acids, tetradecenoic acids, pentadecenoic acids, hexadecenoic acids such as hypogeic acid, heptadecenoic acids, octadecenoic acids such as oleic acid, elaidic acid, nonadecenoic acid, eicosenoic acids, erucic acid, brassidic acid, etc. It is to be understood that the aforementioned unsaturated carboxylic acids are only representative of the type of compounds which may be employed to form the desired esters, and that the present invention is not necessarily limited thereto.

The catalyst which is employed to effect the reduction of the aforementioned acids will comprise a catalyst composite comprising cadmium and rhenium composited on a solid support. In addition, if so desired, the catalyst composite may also contain a noble metal of Group VIII of the Periodic Table also composited on the solid support such as platinum, palladium, ruthenium, rhodium, etc. The cadmium will be present on the solid support, usually in the form of cadmium oxide, in an amount in the range of about 1% to about 10% by weight of the catalyst composite. Likewise, the rhenium which is present on the catalyst composite in any of its oxidation states, an oxidation state lower than +7 being preferred, is present in an amount in the range of from about 0.5% to about 5% by weight of the catalyst composite, while the noble metal, if one is utilized to form the desired catalyst composite, will also be present in a zerovalent state in an amount in the range of from about 0.01% to about 2.5% by weight of the finished composite.

The aforementioned cadmium and rhenium, along with, if so desired, a noble metal of Group VIII of the Periodic Table are composited on the solid support which, in the preferred embodiment of the invention, comprises a relatively high surface area inorganic oxide. Examples of these inorganic oxides will include aluminas such as gamma-alumina, eta-alumina, theta-alumina, silica, or mixtures of inorganic oxides such as alumina-silica, silica-zirconia, silica-magnesia, alumina-silica-zirconium etc.

The reduction catalysts which are used in the process of the present invention may be prepared in any suitable manner. An example of the type of preparation which may be used comprises impregnating the solid support such as gamma-alumina with an aqueous solution of a rhenium-containing composite such as ammonium perrhenate, perrhenic acid, etc. for a period of time which is sufficient to allow the deposition of the desired amount of rhenium on the solid support, that is, an amount sufficient so that the finished catalyst composite will contain from about 0.5 to about 5% of rhenium. After recovery of the impregnated solid support, the composite is then calcined at a temperature in the range of from about 250° to about 750° C. in an air atmosphere for a period of time which may range from about 0.5 up to about 4 hours in duration. The calcined composite is then subjected to a reducing treatment by heating the composite at a temperature within the range hereinbefore set forth in a hydrogen atmosphere. In the event that it is desired to have a noble metal of Group VIII of the Periodic Table also present in the catalyst composite, this metal is co-impregnated with the rhenium utilizing an aqueous solution of a noble metal-containing compound such as chloroplatinic acid, chloropalladic acid, ruthenium chloride, rhodium chloride, etc. Following the co-impregnation, the composite is then treated in a manner similar to that hereinbefore set forth, that is, it is calcined and reduced. As in the case of the rhenium, the co-impregnation with the noble metal is also effected by utilizing a sufficient amount of aqueous solution so that the noble metal will be present in the final catalyst composite in an amount in the range of from about 0.01% to about 2.5% by weight of the finished composite.

The thus formed composite containing rhenium and, if so desired, a noble metal, is thereafter impregnated with a solution of cadmium salt, said cadmium being present in an amount so that the finished catalyst will contain from about 1 to about 10% by weight of cadmium. Examples of cadmium salts which may be employed to effect the impregnation will preferably consist of organic salts of cadmium such as cadmium formate, cadmium acetate, cadmium propionate, etc., although it is also contemplated within the scope of this invention that some inorganic salts of cadmium, such as cadmium chloride, cadmium bromide, cadmium phosphate, etc. may also be employed, although not necessarily with equivalent results. In the preferred embodiment of the invention, the impregnation of the catalyst composite with cadmium is effected under a nitrogen blanket in order to provide an inert atmosphere for the aforesaid impregnation step. After allowing the impregnation with the cadmium salt to be effected for a predetermined period of time, which may range from about 0.5 up to about 4 hours or more in duration, the resultant composite is then recovered and calcined under a nitrogen blanket at a temperature in the range of from about 250° to about 400° C. to form cadmium oxide. Upon completion of the calcination period, the resulting composite which forms the catalyst may be utilized in the reduction process of the present invention.

It is also contemplated within the scope of this invention that the catalyst which is used in the process of the present invention may be prepared in a continuous manner of operation. When such a type of operation is employed, the solid support material comprising an inorganic oxide which may be of any desired shape such as pellets, spheres, globules, rods, etc. is continuously passed through an aqueous solution of rhenium at a predetermined rate of speed in order that the predetermined amount of rhenium may be impregnated on the support. The support after passage through the solution is continuously withdrawn and passed to a calcination zone wherein it is treated at an elevated temperature, in the presence of air, within the range hereinbefore set forth. After completion of the calcination period, the rhenium impregnated material is then, if so desired, passed through a second impregnating bath wherein the noble metal of the Group VIII Periodic Table is deposited thereon. Alternatively, it is also contemplated that the noble metal and the rhenium may be co-impregnated in a single impregnation zone following which the impregnated solid support is calcined and thereafter subjected to a reducing step in which the impregnated support is continuously passed through a reducing zone at an elevated temperature while being subjected to a hydrogen flow. After passage through the reducing zone, the metal impregnated solid support is continuously withdrawn and passed to a different impregnation zone wherein the composite is impregnated with cadmium utilizing a cadmium salt of the type previously discussed. The impregnation of the composite with cadmium is also effected at an elevated temperature in the presence of nitrogen for a period of time sufficent to deposit the desired amount of cadmium on the composite. The cadmium treated composite is then continuously withdrawn and passed to a second calcination zone where it is also calcined at an elevated temperature in the presence of nitrogen to form cadmium oxide. After passage through this latter calcination zone, the desired composite is continuously withdrawn and recovered.

The reduction process of the present invention which results in the obtention of esters and alcohols which still possess the unsaturation of the starting materials and which are recovered in an amount greater than that which was hereinbefore obtained may be effected in either a batch or continuous type operation. When utilizing a batch type operation, a quantity of the unsaturated carboxylic acid, which is used to undergo esterification or to obtain an alcohol, is placed in an appropriate apparatus which is pressure resistant in nature, such as an autoclave of the rotating, mixing or stirring type. In addition, the particular catalyst hereinbefore described is also added to the apparatus in an amount in the range of from about 25:1 to about 5:1 grams of acid per gram of catalyst. After pressuring the apparatus to an initial operating pressure, the apparatus is then heated to the desired operating temperature and maintained thereat for a predetermined period of time. The operating conditions which are employed to effect the desired reduction process will include a temperature in the range of from about 100° to about 500° C. and superatmospheric pressures ranging from about 100 to about 5000 psi for a period of time which may range from about 0.5 up to about 10 hours or more in duration, the reaction time being determined by the particular unsaturated carboxylic acid undergoing reduction or preparation of an alcohol as well as the reaction temperature and amount of pressure which is employed during the reaction. The superatmospheric pressures which are employed may be afforded by hydrogen alone or, if so desired, the amount of hydrogen present may afford only a partial pressure, the remainder of the desired operating pressure being afforded by the presence of an inert gas such as nitrogen, helium, argon, etc. in the reaction apparatus. During the reaction period, a predetermined amount of hydrogen is continuously bled from the reaction vessel, the water which is formed as a side product during the reaction being removed along with the hydrogen. The amount of hydrogen which is bled from the reaction apparatus will be dependent upon the amount charged, said amount which is recovered being sufficient enough to maintain the desired operating pressure at a predetermined level. Upon completion of the desired reaction period, the hydrogen charge is discontinued as is the heat treatment, and after the reaction vessel or apparatus has returned to room temperature, the excess pressure is discharged, the apparatus is opened, and the reaction mixture is recovered therefrom. The thus recovered mixture may then be filtered through a solid adsorbent to separate the catalyst from the reaction product, the latter then being subjected to conventional means of separation to recover the desired ester and/or alcohol.

It is also contemplated within the scope of this invention that the reduction process may be effected in a continuous manner of operation. When such a type of operation is employed, a reaction vessel containing the reduction cyatalyst is maintained at the proper operating conditions of temperature and pressure, the unsaturated carboxylic acid which is to undergo reduction is continuously charged to the reaction vessel where it is contacted with the catalyst in the presence of hydrogen which is also continuously charged to the reactor. After passage through the reaction vessel for a predetermined period of time, the reactor effluent is continuously withdrawn from the reaction vessel and subjected to conventional means of separation whereby the desired ester or alcohol of the unsaturated carboxylic acid, which still possesses the unsaturation of the starting material, is separated and recovered, while any unreacted starting materials, both gaseous and liquid in nature, after being dried to remove the water formed during the reaction, are recycled to the reaction vessel to form a portion of the feedstock.

It is contemplated that the continuous method of operation may be effected in various ways. For example, the reduction catalyst may be positioned in the reaction vessel as a fixed bed, and the unsaturated carboxylic acid undergoing reduction or preparation of an alcohol is passed over the bed in either an upward or downward flow. Another method of effecting the reaction is to employ the catalyst as a moving bed in the reaction vessel and having the unsaturated carboxylic acid and the catalyst pass through the reaction vessel either cncurrently or countercurrently to each other. Likewise, if so desired, a slurry-type of operation may be employed in which the reduction catalyst is carried into the reaction vessel as a slurry in the unsaturated carboxylic acid.

The following examples are given to illustrate the process of this invention. However, it is to be understood that the examples are given merely for purposes of illustration and that the present invention is not necessarily limited thereto.

EXAMPLE I

A catalyst was prepared by impregnating 125 grams of alumina with an aqueous solution containing 1.8 grams of ammonium perrhenate. Following the impregnation, the composite was calcined at a temperature of 500° C. for a period of 1 hour in an air atmosphere and thereafter reduced in a hydrogen atmosphere at a temperature of 500° C. for a period of 1 hour, the resulting composite containing 1% of rhenium on the support. Thereafter, the rhenium composite was steam impregnated with a solution of cadmium acetate for a period of 4 hours. The cadmium-impregnated composite was then calcined at a temperature of 275° C. for a period of 3 hours under a nitrogen atmosphere, the finished composite containing 7% of cadmium oxide on the composite.

A feedstock comprising 200 grams of oleic acid and 10 grams of the catalyst prepared according to the above paragraph was charged to a one liter stirred autoclave which was then sealed and flushed twice with hydrogen. The autoclave was then pressured to 100 psig with hydrogen and heated to a temperature of 325° C. Upon reaching the desired operating temperature, the autoclave was further pressurized to 750 psig with hydrogen, and the reaction was allowed to proceed for a period of 3 hours, while maintaining the temperature at about 325° C. and a pressure of 750 psig. During the 3 hour reaction period, hydrogen was bled from the autoclave at a rate of one $ft^3/hr$, while stirring the autoclave at a rate of 1100 rpm. In addition, a sufficient amount of hydrogen was charged to the autoclave to maintain the aforesaid pressure. At the end of the 3 hour period, heating was discontinued and, after the autoclave had returned to room temperature, the excess pressure was vented and the autoclave was opened. The reaction mixture which was recovered from the autoclave was dissolved in hot toluene and filtered through a solid adsorbent to remove the catalyst. A portion of the product was stripped of the toluene to obtain a white solid reaction product. Analysis of the product disclosed that there had been a 97% conversion of the oleic acid to esters and alcohols including oleyl oleate, oleyl alcohol as well as geometric and positional isomers thereof with only a 16% saturation of the double bond. The selectivity as measured by the percent of acid conversion divided by the percent of double bond saturation was 6.1.

EXAMPLE II

In this example, a catalyst was prepared by co-impregnating alumina spheres with ammonium perrhenate and chloroplatinic acid for a period of 4 hours with steam. At the end of this time, the impregnated alumina was calcined at a temperature of 500° C. for a period of 1 hour followed by reduction in a hydrogen atmosphere for an additional period of 1 hour at the same temperature. The resulting composite contained 1% rhenium and 0.1% platinum. This composite was then further steam impregnated with a cadmium acetate solution for a period of 4 hours and the thus impregnated composite was calcined at a temperature of 275° C. under a nitrogen blanket. The final catalyst composite contained 7% cadmium oxide along with the 1% rhenium and 0.1% platinum.

A reduction reaction was effected by charging 200 grams of oleic acid and 10 grams of the catalyst composite prepared according to the above paragraph to a one liter stirred autoclave. The autoclave was flushed with hydrogen, sealed and pressured to 100 psig with hydrogen. Following the heating of the autoclave to a temperature of about 325° C., it was further pressured with hydrogen and stirred at a rate of 1100 rpm. The reaction was allowed to proceed for a period of two hours at a temperature of 325° C. while bleeding hydrogen from the autoclave at a rate of one cubic foot per hour and charging a sufficient amount of hydrogen to the autoclave to maintain a pressure of 750 psig. At the end of the two hour period, heating was discontinued and after the autoclave had returned to room temperature, any excess pressure was vented and the autoclave was opened. The reaction product was recovered and treated in a manner similar to that hereinbefore set forth. Analysis of the product disclosed that there had been a 95% conversion of the oleic acid predominantly esters and alcohols including oleyl oleate, oleyl alcohol as well as geometric and positional isomers thereof with a 28% saturation of the double bond, the selectivity in this experiment being 3.4.

EXAMPLE III

In this example, a catalyst comprising 1% rhenium, 0.1% platinum, and 10% cadmium oxide was prepared in a manner similar to that hereinbefore set forth in the above examples. The catalyst was used in the treatment of oleic acid with hydrogen under conditions similar in nature to those hereinbefore set forth. Analysis of the reaction product, after a reaction period of two hours showed that there had been a 93% conversion of oleic acid to the ester and alcohols with a 25% saturation of the double bond, thus giving a selectivity of 3.7.

EXAMPLE IV

To illustrate the unexpected degree of selectivity which is obtained when using the process of the present invention which involves the use of a bleed during the reaction period, a catalyst was prepared by coimpregnating alumina in the form of spheres with an aqueous solution containing 1% rhenium to weight of alumina as ammonium perrhenate and 0.1% of platinum to weight of alumina as chloroplatinic acid. The steam impregnation was allowed to proceed for a period of 4 hours following which the impregnated alumina spheres were calcined at a temperature of about 500° C. for a period of 1 hour in an air atmosphere. Following the calcination, the impregnated spheres were then further heated at a temperature of 500° C. for an additional period of 1 hour in a hydrogen atmosphere to reduce the rhenium and platinum. Following this, the composite was then steam impregnated with a solution of cadmium acetate for a period of 4 hours. Thereafter, the cadmium impregnated deposit was calcined at a temperature of about 275° C. for a period of about 1 hour under a nitrogen atmosphere whereby cadmium oxide was formed on the composite.

The feedstock comprising 200 grams of oleic acid and 10 grams of the catalyst prepared according to the above paragraph was charged to a 1 liter stirred autoclave, which was then sealed and flushed twice with hydrogen. The autoclave was then pressured to 100 psig with hydrogen and heated to a temperature of 300° C. Upon reaching the desired operating temperature, the autoclave was further pressured to 1000 psig. The reaction was allowed to proceed for a period of 4 hours while maintaining the temperature at about 300° C. and a pressure of 1000 psig, the autoclave being stirred at a rate of 1100 rpm. At the end of the 4 hour period, heating was discontinued and after the autoclave had returned to room temperature the excess pressure was vented, and the autoclave opened. The reaction mixture was dissolved in hot toluene and filtered through a solid absorbent to remove the catalyst. A portion of the product was stripped to obtain a white solid reaction product. Analysis of the product by iodine value disclosed that there had been a 44% double bond saturation, while quantitative gas chromatography showed a 98% conversion of the oleic acid to esters and alcohols; the selectivity, measured by the percent of acid conversion divided by the percentage of double bond saturation being 2.2.

It is evident that a comparison of the results obtained in this example with those obtained in Examples I, II and III above discloses that a selectivity to the desired unsaturated product when utilizing a hydrogen bleed during the reaction is significantly greater than the selectivity which is obtained when using a conventional reduction process.

EXAMPLE V

A reduction catalyst containing rhenium and palladium along with cadmium oxide composited on a gamma-alumina support may be used in the treatment of crotonic acid with hydrogen in an autoclave utilizing reaction conditions which include a temperature of 150° C. and a pressure of 1000 psig, the hydrogen being continuously bled from the autoclave during the reaction period in an amount sufficient to maintain the aforesaid pressure. Upon completion of the required reaction period, the autoclave, after being allowed to return to room temperature, may be opened and the reaction product recovered, the desired crotonyl crotonate and crotonyl alcohol being separated and recovered.

In like manner, other unsaturated carboxylic acids such as hypogeic acid, erucic acid and hexenoic acid may be treated with hydrogen in the presence of similar catalyst composites at operating conditions of temperature and pressure similar to those hereinbefore set forth in the above examples. In addition, hydrogen is continuously bled from the reactor in an amount sufficient to maintain the desired operating pressure within the ranges previously discussed. The desired reaction products comprising hypogeyl hypogeate, hypogeyl alcohol, erucyl erucate, erucyl alcohol, hexenyl hexenate, hexenyl alcohol as well as geometric and positional isomers thereof may be recovered from the reaction mixture.

We claim as our invention:

1. A process for the reduction of an unsaturated carboxylic acid comprising treating an unsaturated carboxylic acid in a reaction system in the presence of hydrogen and a reduction catalyst comprising cadmium and rhenium composited on a solid support at treatment conditions, continuously bleeding hydrogen from said reaction system during the reaction period, and recovering the resultant unsaturated product.

2. The process as set forth in claim 1 in which said treatment conditions include a temperature in the range of from about 100° to about 500° C., and a pressure in the range of from about 100 to about 5000 pounds per square inch.

3. The process as set forth in claim 1 in which said catalyst also contains a noble metal of Group VIII of the Periodic Table.

4. The process as set forth in claim 1 in which said solid support comprises a high surface area alumina.

5. The process as set forth in claim 4 in which said high surface area alumina is gamma-alumina.

6. The process as set forth in claim 4 in which said noble metal is platinum.

7. The process as set forth in claim 1 in which said unsaturated carboxylic acid is oleic acid and said unsaturated product is oleyl oleate, oleyl alcohol and geometric and positional isomers thereof.

8. The process as set forth in claim 1 in which said unsaturated carboxylic acid is crotonic acid and said unsaturated product is crotonyl crotonate and crotonyl alcohol.

9. The process as set forth in claim 1 in which said unsaturated carboxylic acid is hypogeic acid and said unsaturated product is hypogeyl hypogeate, hypogeyl alcohol and geometric and positional isomers thereof.

10. The process as set forth in claim 1 in which said unsaturated carboxylic acid is erucic acid and said unsaturated product is erucyl erucate, erucyl alcohol and geometric and positional isomers thereof.

11. The process as set forth in claim 1 in which said unsaturated carboxylic acid is hexenoic acid and said unsaturated product is hexenyl hexenate and hexenyl alcohol.

* * * * *